US012605220B2

(12) United States Patent
Crews et al.

(10) Patent No.: US 12,605,220 B2
(45) Date of Patent: Apr. 21, 2026

(54) FLUSHING IMPROVEMENTS FOR ROBOTIC SURGICAL TOOL CLEANING

(71) Applicant: Cilag GmbH International, Zug (CH)

(72) Inventors: Andrew O. Crews, Maineville, OH (US); James A. Vandewalle, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 133 days.

(21) Appl. No.: 18/773,674

(22) Filed: Jul. 16, 2024

(65) Prior Publication Data

US 2025/0025246 A1    Jan. 23, 2025

Related U.S. Application Data

(60) Provisional application No. 63/528,209, filed on Jul. 21, 2023.

(51) Int. Cl.
*A61B 34/30* (2016.01)
*A61B 90/00* (2016.01)

(52) U.S. Cl.
CPC ...... *A61B 34/30* (2016.02); *A61B 2090/0813* (2016.02)

(58) Field of Classification Search
CPC . A61B 34/30; A61B 2090/0813; A61B 90/70; A61B 2090/701; A61B 17/00234; A61B 17/29
See application file for complete search history.

(56) References Cited

U.S. PATENT DOCUMENTS

| | | | |
|---|---|---|---|
| 2021/0007828 A1 * | 1/2021 | Radermacher | A61B 34/70 |
| 2022/0240967 A1 * | 8/2022 | Ushpizin | A61B 17/16 |

* cited by examiner

*Primary Examiner* — Natasha N Campbell
(74) *Attorney, Agent, or Firm* — Joshua D. Young

(57) ABSTRACT

A robotic surgical tool that includes a plate inside of a drive housing. The drive housing is divided into an upper portion and lower portion by the plate. Extending from the drive housing is an elongate shaft. The robotic surgical tool also includes an injection port that passes a cleaning fluid into the drive housing. Inside the drive housing there is a diverter adjacent to the injection port. The diverter has a ramp which can direct fluid from the injection port to the upper portion of the drive housing.

20 Claims, 6 Drawing Sheets

FLUSHING IMPROVEMENTS FOR ROBOTIC SURGICAL TOOL CLEANING

PRIORITY

This application claims priority to U.S. Provisional Pat. App. No. 63/528,209, filed on Jul. 21, 2023.

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

Robotic surgical tools typically include a drive housing and a shaft that extends from the drive housing. The end effector is positioned at the end of the shaft and the wrist interposes the end effector and the end of the shaft to facilitate articulation of the end effector. The drive housing includes coupling features that releasably couples the surgical tool to a robotic surgical system, and houses various drive inputs and mechanisms (e.g., gears, actuators, etc.) designed to control operation of various features associated with the end effector.

After use, the drive housing and other component parts of the surgical tool must be fully cleaned and disinfected. One method of cleaning the drive housing and other components is to inject a cleaning fluid into the device so that debris and contaminants can be flushed out. However, flushing can be inefficient if the fluid does not reach certain areas within the device. Instead of debris being flushed out of the device the contaminant can trapped and collect in the areas within the device that the cleaning fluid doesn't reach. Since proper and effective cleaning is vital for the health of patients, there is an ongoing need for improvements to the cleaning processes of robotic surgical tools.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to improvements made to improve the fluid flow within the device to increase the efficiency of the cleaning and disinfecting process.

Embodiments disclosed herein describe an improved surgical tool that increases the efficiency of a flushing process for cleaning and sterilizing the tool after a procedure. One possible improvement is the inclusion of a dual flush port for injecting a cleaning fluid into the device to expel debris and contaminants. One flush port is dedicated to flushing the drive housing while the other is for cleaning the shaft and distal end of the surgical tool. Another possible improvement is the addition of a passive fluid diverter (PFD). The PFD directs fluid flow from the flush port and directs it to a specific region of the housing. Another possible improvement is the addition of one or more additional flush ports on the proximal side of the drive housing to increase flow and turbulence which aid in the flushing process. This proximal flush port(s) can also aid in the draining of the fluid upon completion of the flushing process. Features on the drive housing may further be angled or sloped towards the proximal ports to help facilitate the draining process and prevent fluid from being retained. Another possible improvement is the addition of a retention lip on one or more components of the surgical tool to limit the fluid loss during the flushing process.

Figure 1:
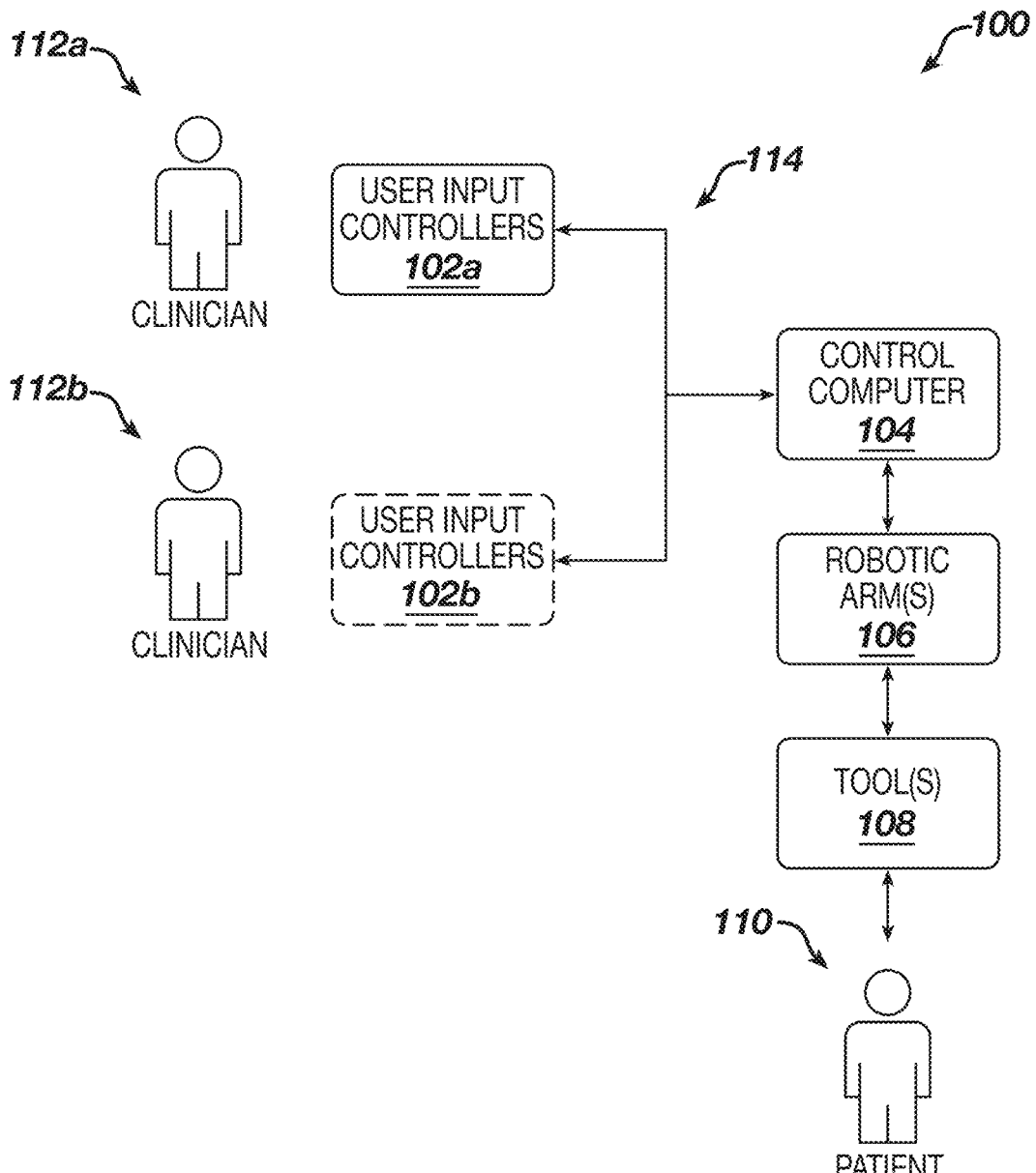
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the robotic surgical system 100 portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed lines) may be operated by a second clinician 112*b* to direct operation of the robotic arms 106 and tools 108 in conjunction with the first clinician 112*a*. In such embodiments, each clinician 112*a,b* may control different robotic arms 106 or, in some cases, complete control of the robotic arms 106 may be passed between the clinicians 112*a,b*. In some embodiments, additional robotic manipulators (not shown) having additional robotic arms (not shown) may be utilized during surgery on the patient 110, and the additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) and according to any communications protocol.

The user input controllers 102*a,b* generally comprise one or more physical controllers that can be grasped or handled by the clinician 112*a,b* and manipulated in space while viewing the procedure via a stereo display. The physical controllers can comprise manual input devices movable in multiple degrees of freedom, and often include an actuatable handle or pedal for actuating the surgical tool(s) 108. The control computer 104 can also include an optional feedback meter viewable by the clinician 112*a,b* via a display to provide a visual indication of various surgical instrument metrics, such as the amount of force being applied to the surgical instrument (i.e., a cutting instrument or dynamic clamping member).

Figures 2, 3:
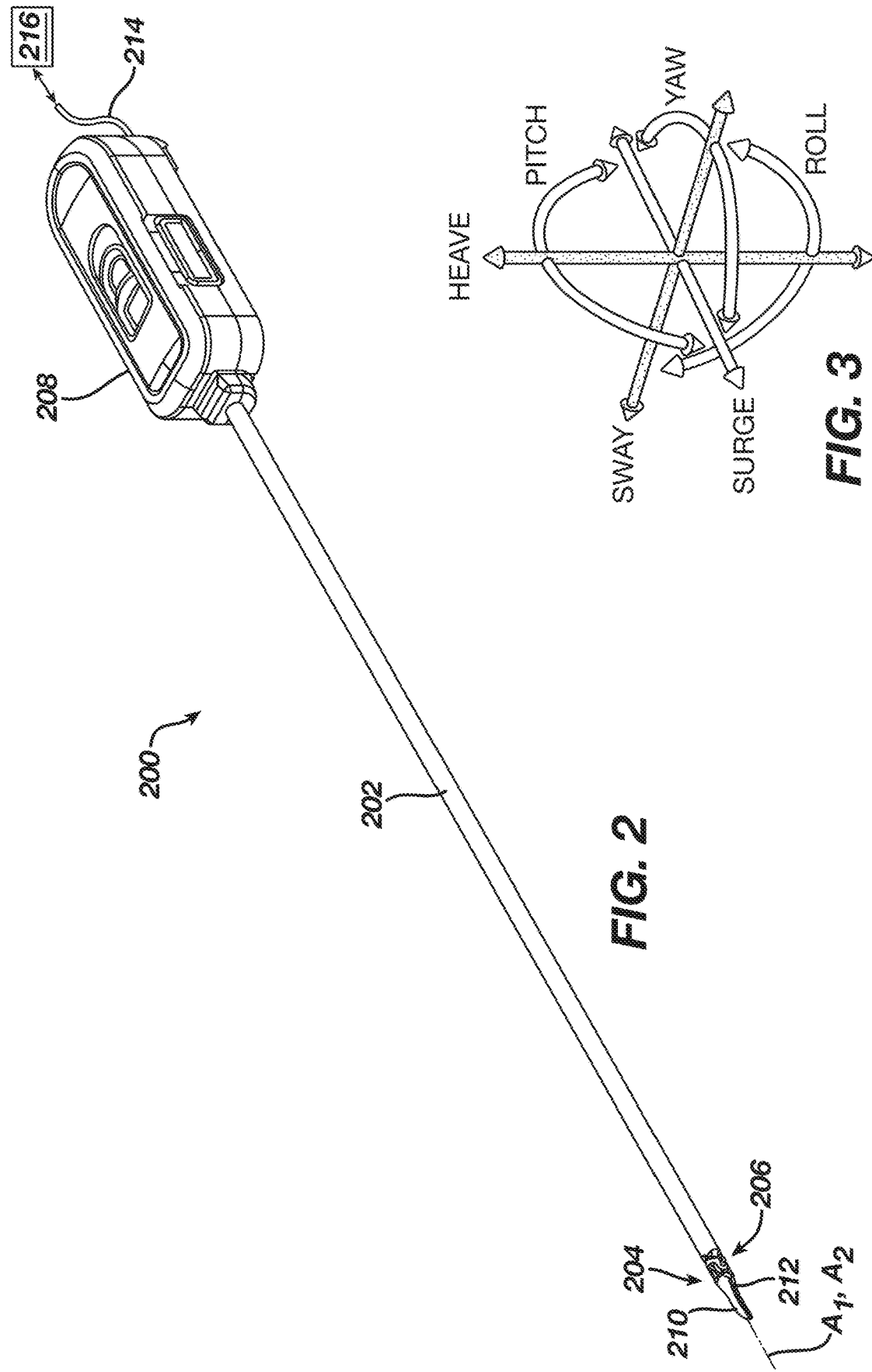
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) or translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In robotic surgical systems, the drive housing 208 can include coupling features that releasably couple the surgical tool 200 to a robotic surgical system (e.g., the robotic arm 106 of FIG. 1).

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, drive members, etc.) designed to control operation of various features associated with the end effector 204 (e.g., clamping, firing, rotation, articulation, cutting, etc.). In at least some applications, the shaft 202 and the end effector 204 coupled thereto are configured to rotate about a longitudinal axis $A_1$ of the shaft 202. In such embodiments, at least one of the drive inputs controls rotational movement of the shaft 202 about the longitudinal axis $A_1$.

The end effector 204 may comprise, but is not limited to, forceps, a grasper, a needle driver, scissors, an electro cautery tool, a vessel sealer, a stapler, a clip applier, a hook, a spatula, a suction tool, an irrigation tool, an imaging device (e.g., an endoscope or ultrasonic probe), or any combination thereof. In the illustrated embodiment, the end effector 204 comprises a tissue grasper and vessel sealer that includes opposing jaws 210, 212 configured to move (articulate) between open and closed positions. As will be appreciated, however, the opposing jaws 210, 212 may alternatively form part of other types of end effectors such as, but not limited to, surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot relative to the other to open and close the jaws 210, 212. The principles of the present disclosure, however, are equally applicable to end effectors without opposing jaws. In some embodiments, the surgical tool 200 may further be configured to apply energy to tissue, such as radio frequency (RF) energy.

FIG. 3 illustrates the potential degrees of freedom in which the wrist 206 may be able to articulate (pivot). The wrist 206 comprises a joint configured to allow pivoting movement of the end effector 204 relative to the shaft 202. The degrees of freedom of the wrist 206 are represented by three translational variables (i.e., surge, heave, and sway) and three rotational variables (i.e., Euler angles or roll, pitch, and yaw). The translational and rotational variables describe the position and orientation of the end effector 204 with respect to a given reference Cartesian frame. "Surge" refers to forward and backward translational movement, "heave" refers to translational movement up and down, and "sway" refers to translational movement left and right. "Roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system that facilitates movement and articulation of the end effector 204 relative to the shaft 202. Moving (actuating) the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the drive housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204. The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204.

After the surgical tool 200 has been placed in service, it must be properly cleaned in preparation for future use. Because of the several moveable component parts contained within the drive housing 208, properly cleaning the internal components of the drive housing 208 can be a complex and time-consuming process. According to the present disclosure, improvements are disclosed that promote fluid flow within the device to increase the efficiency of the cleaning and disinfecting process.

Figure 4:
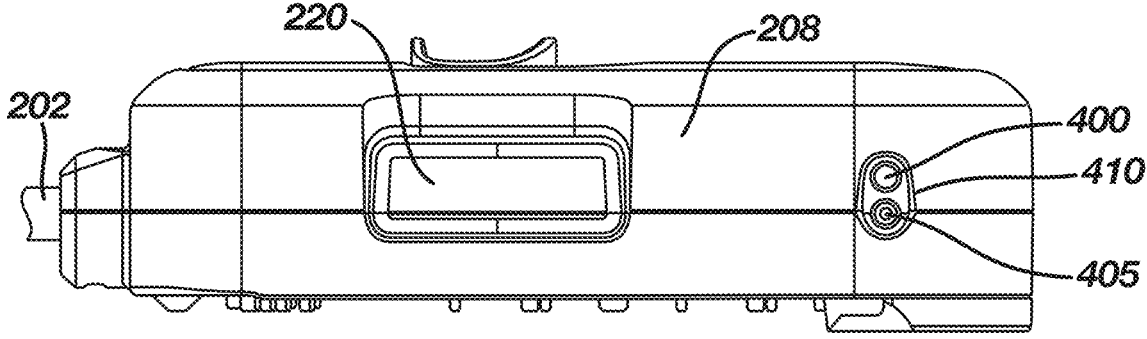
FIG. 4 is side view of an example robotic surgical tool, that may incorporate some or all of the principles of the present disclosure.

FIG. 4 is a side view of drive housing 208. In the side wall of drive housing 208 is a port 410 which may contain a distal port 400 and proximal port 405. After a surgical procedure the surgical tool may be reprocessed and cleaned for future use. During cleaning a technician may inject a cleaning fluid through one or both ports to flush out any internal debris or contamination. The injection of the cleaning fluid may be done by hand with a syringe or may be done with an automated pump to cycle the cleaning fluid through the surgical tool. Distal port 400, directs the cleaning fluid into drive housing 208, while proximal port 405 directs the cleaning fluid into shaft 202 and out to wrist 206 and end effector 204. In another embodiment, the roles of distal port 400 and proximal port 405 may be reversed.

The cleaning solution used may comprise any aqueous fluid configured to clean and disinfect the inner component parts of the drive housing. Example cleaning solutions include detergents such as, but are not limited to, Prolystica® 2× enzymatic detergent and Neodisher MediClean Forte.

To clean the surgical tool, the technician may inject the cleaning fluid into distal port 400 and proximal port 405 until the entire drive housing is filled with the cleaning fluid. During the flushing process debris and contaminants are flushed out of the surgical tool through either dedicated drains or natural gaps between components of the surgical tool and the drive housing 208 all the while new cleaning fluid is continually injected into distal port 400 and proximal port 405. Then after a period of time of being exposed to the cleaning fluid, the technician disconnects the fluid from distal port 400 and proximal port 405 and allows the fluid within housing 208, shaft 202, wrist 206, and end effector 204 to drain.

Figure 5:
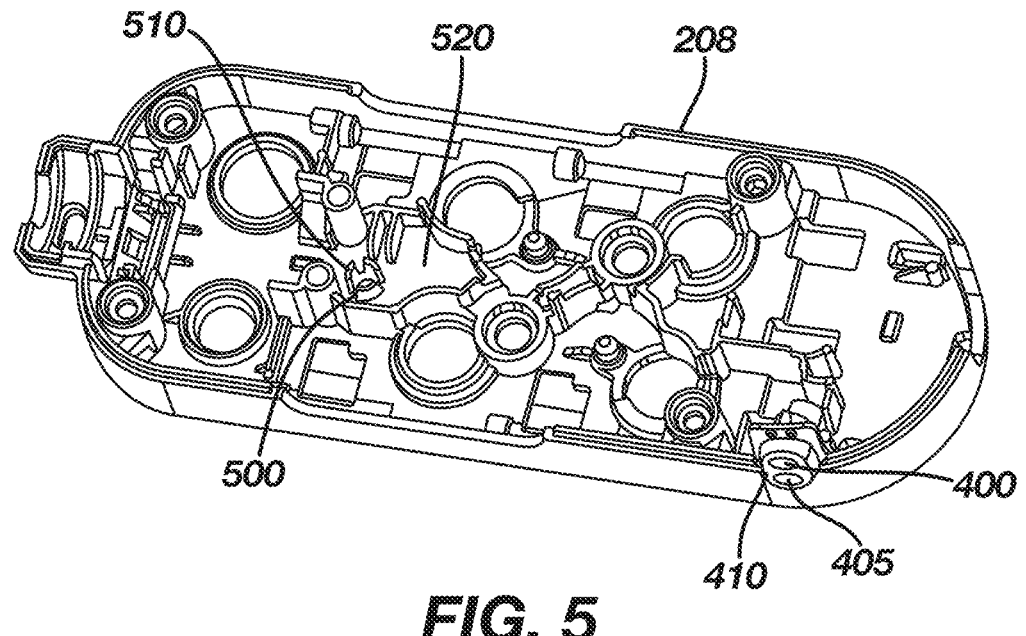
FIG. 5 is an isolated view of a portion of a drive housing for a robotic surgical tool, that may incorporate some or all of the principles of the present disclosure.

In some embodiments, as illustrated in FIG. 5, the drive housing 208 may provide one or more additional ports on the proximal side of drive housing 208. In addition to the dual port 410 a third port 500 is provided with dual functionality. Third port 500 can be a third input for the injection of the cleaning fluid during the flushing process. Third port 500 serves as a second injection port in addition to the distal port 400 to deliver cleaning fluid within the drive housing. The drive housing contains many parts with different shapes, contours and surfaces, some of which are narrowly spaced apart. Adding an additional input for injecting cleaning fluid into drive housing 208 increases fluid flow and increases turbulent fluid flow which boost the flushing efficiency. Third port 500 also serves as a drain for fluid and contaminants to exit once the flushing process is over. After the flushing process has ended, and the technician removes the fluid flow from the input ports on the surgical tool, third port 500 acts as a drain and allows any remaining fluid or debris to exit drive housing 208. Further, a drain plate 520 may be added to aid in the draining process. Drain plate 520 is smooth surface that is angled towards third port 500 so that when fluid is draining from drive house 208, the fluid along with any contaminants is funneled towards third port 500 to drain. Third port may also have one or more fingers 510. Fingers 510 increase fluid flow during flushing by providing exposed recesses circumferentially around third port 500 which allow the fluid to flow through drive housing 208. Likewise, fingers 510 promote draining after the flushing process by giving the fluid and contaminants a series of recesses circumferentially around third port 500 through which the fluid may flow back out of drive housing 208.

Figures 6, 7:
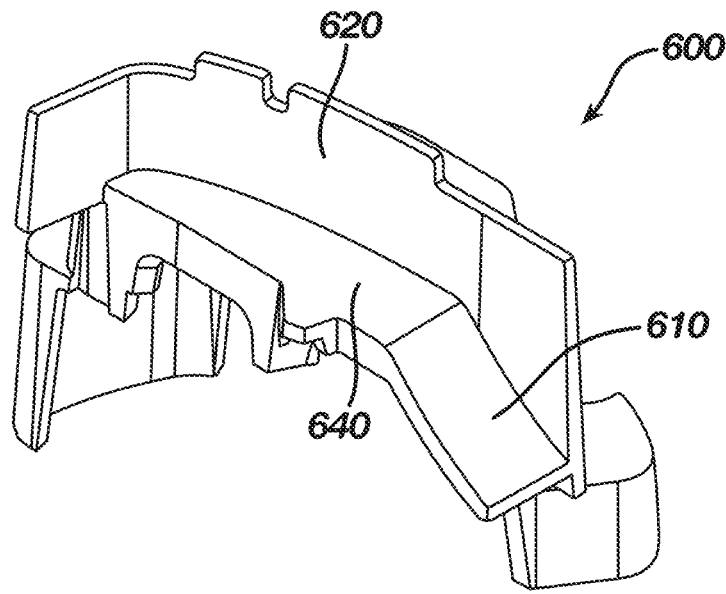
FIG. 6 is a fluid diverter, according to one or more additional embodiments
FIG. 7 depicts a portion of the drive housing containing a fluid diverter of FIG. 6, according to one or more additional embodiments.

As described above, the drive housing contains many parts with different shapes, contours, and surfaces, some of which are narrowly spaced apart. It is therefore desirable to direct the cleaning fluid being injected into drive housing 208 as opposed to openly injecting fluid into the cavity and allowing the fluid to find its own path with drive housing 208. A passive fluid diverter (PFD) 600, as shown in FIG. 6, may be used within drive housing 208 to direct the fluid. PFD 600 has a ramp 610 which diverts the injected fluid up into the upper half of drive housing 208. The cleaning fluid travels up ramp 610 to flat 640 and is retained and directed approximately ninety degrees by retaining wall 620.

FIG. 7 shows PFD 600 assembled into drive housing 708. As cleaning fluid is injected into distal port 700 it immediately hits ramp 610 and directed to the upper half of drive housing 708 onto flat 640. Once on flat 640 the cleaning fluid is retained along wall 620 and then directed approximately ninety degrees in a direction towards shaft 202 at which point it propagates throughout drive housing 708. It is desirable to get the cleaning fluid into the upper half of the drive housing as quickly as possible because of the dense interior of the drive housing and because fluid will follow gravity it is easier for the cleaning fluid to work its way down from the upper half of drive housing 708 than fight its way up from the lower half of drive housing 708.

Figure 8:
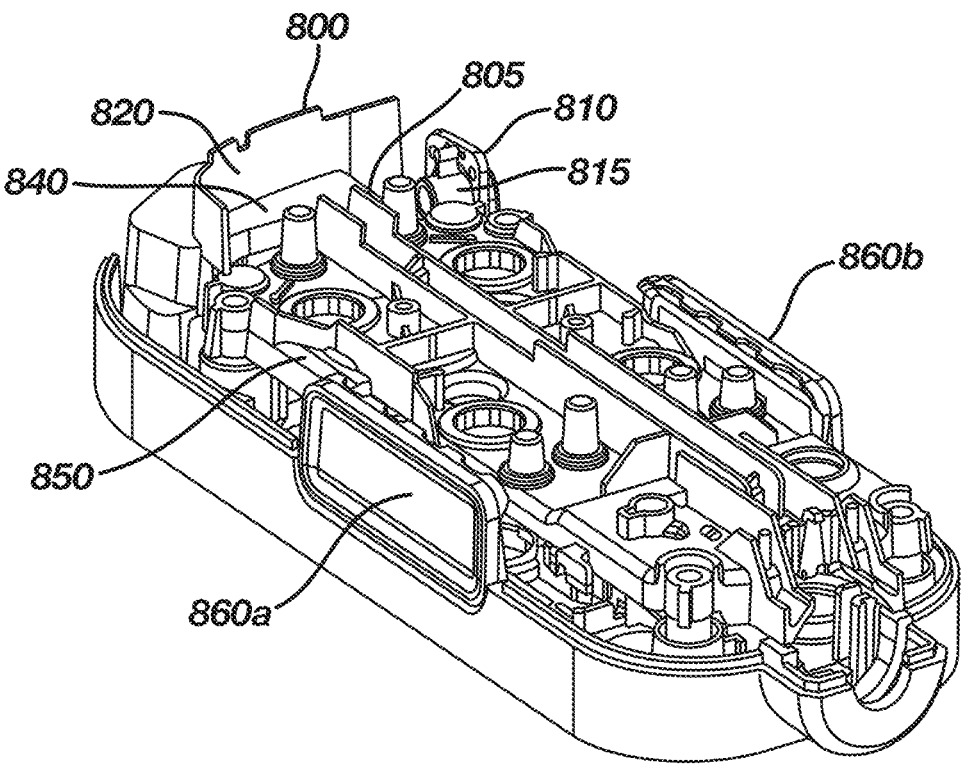
FIG. 8 is an isolated view of an alignment plate mounted on the drive housing of FIG. 7, according to one or more additional embodiments.

As illustrated in FIG. 8, drive housing 208 may contain an alignment plate 850. Alignment plate 850 essentially divides the lower and upper halves of drive housing 208. PFD 800 diverts the cleaning fluid from distal port 815 and raises the fluid up above alignment plate 850. As described earlier PFD then retains and redirects the cleaning fluid into the rest of drive housing 208. The cleaning fluid is flushed over the top of alignment plate 850 and can more easily reach the furthest end of drive housing 208 from the dual port 810. While flushing over the top of alignment plate 850 the cleaning fluid will permeate its way down to the lower half of the drive housing through the natural gaps between components of the surgical tool. Additionally, not shown, third port 500 may be injecting fluid into the lower half of drive housing 208 while PFD 800 directs cleaning fluid to flush over the top half of drive housing 208. As discussed above, there are natural gaps between components within drive housing 208. These gaps provide an outlet for fluid to escape, while the fluid is meant to drain and eventually exit drive house 208 along with the debris and contamination, there are areas of leakage that will hinder the flushing process and decrease its efficiency. Two of these areas are around release latches 860a and 860b. There are openings between release latches 860a and 860b and drive housing 208. Accordingly, fluid will begin to leak out of these openings and slow down the fluid flow decreasing the flushing process.

Figure 9:
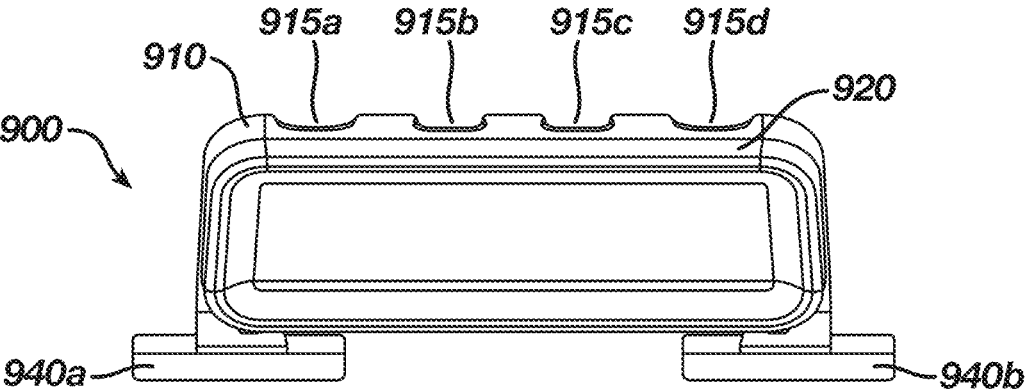
FIG. 9 is an isolated view of a release latch mechanism, that may incorporate some or all of the principles of the present disclosure.

FIG. 9 shows the addition of an inner lip 910 to release latch 900. Inner lip 910 extends inward from exterior 920 and helps minimize leakage around release latch 900. Inner lip 910 may include a scalloped distal edge with one or recesses 915a, 915b, 915c, and 915d. Since inner lip protrudes inward from exterior 920, recesses 915a, 915b, 915c, and 915d in inner lip 910 allow for release latch 900 to be squeezed in to housing 208 about pivots 940a and 940b without contacting any other internal components of the surgical tool, allowing the surgical tool to be removed from robotic surgical system interface.

Figure 10:
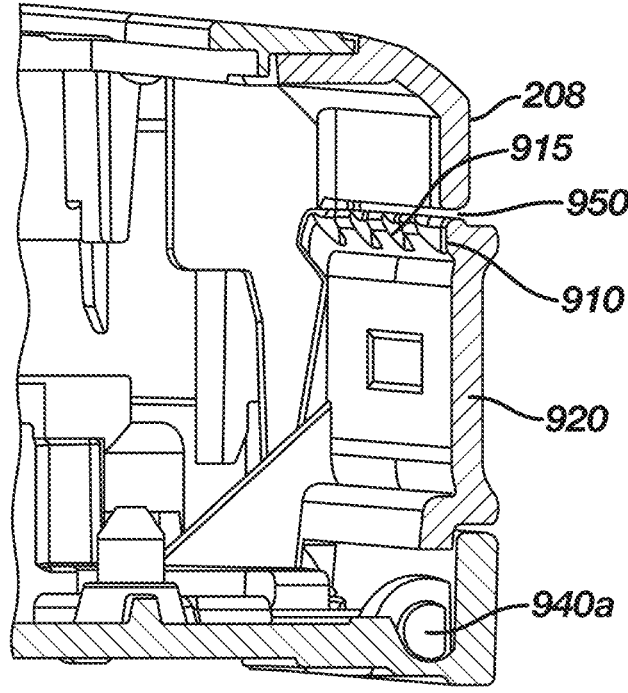
FIG. 10 depicts a portion of the drive housing containing the release latch mechanism of FIG. 9, according to one or more additional embodiments.

FIG. 10 is a cross-sectional view of release latch 900 from FIG. 9 assembled with drive housing 208. Release latch 900 rotates about pivot 940a and 940b (not shown). Gap 950 created between exterior 920 and drive housing 208 is minimized by inner lip 910 with recesses 915 (915a, 915b, 915c, 915d).

Embodiments disclosed herein include:

A. A robotic surgical tool that includes a plate, a drive housing that is divided into an upper portion and lower portion by the plate, an elongated shaft extending from said drive housing, an injection port that passes fluid into the drive housing, and a diverter inside the drive housing adjacent to the injection port, wherein the diverter has a ramp to direct fluid from the injection port to the upper portion of the drive housing.

B. A method of cleaning a robotic surgical tool that includes attaching an injection mechanism to an injection port that passes fluid into the surgical tool, injecting a fluid into the surgical tool through the port. The surgical tool includes, a plate, a drive housing, divided into an upper portion and lower portion by the plate an elongated shaft extending from the drive housing, and a diverter inside the drive housing adjacent to the injection port, the diverter including a ramp. The method further includes diverting the fluid from the injection port with the ramp to the upper portion of the drive housing, filling the upper portion and lower portion of the drive housing with fluid from the injection port, and draining the cleaning solution from the drive housing.

Each of embodiments A and B may have one or more of the following additional elements in any combination: Element 1 wherein the injection port is a dual injection port. Element 2: wherein the dual injection port has a first port and second port. Element 3: wherein the first port and second port are in the lower portion of the drive housing. Element 4: wherein the first port passes fluid into the drive housing and the second port passes fluid into the elongated shaft. Element 5: wherein the second port is below the ramp and the first port is above the ramp. Element 6: wherein the diverter has a flat portion contained within the upper portion of the drive housing and coupled to the ramp. Element 7: wherein the diverter has a wall adjacent to and extending above the ramp and said flat portion. Element 8: wherein the wall has a curve that wraps around the flat portion opposite of the ramp. Element 9: wherein the curve portion is between forty-five and one hundred and thirty-five degrees. Element 10: further comprising a third port that passes fluid into the drive housing. Element 11: wherein the third port is orthogonal to said first port and second port. Element 12: wherein third port also serves as a drain for draining the fluid.

By way of non-limiting example, exemplary combinations applicable to A, and B include: Element 1 with Element 2; Element 2 with Element 3; Element 3 with Element 4; Element 4 with Element 5; and Element 5 with Element 6; Element 7 with Element 8; Element 8 with Element 9; Element 9 with Element 10; Element 11 with Element 12.

What is claimed is:

1. A robotic surgical tool, comprising:
a plate;
a drive housing, divided into an upper portion and lower portion by the plate;
an elongated shaft extending from said drive housing;
an injection port that passes fluid into the drive housing; and
a diverter inside the drive housing adjacent to the injection port,
wherein the diverter has a ramp to direct fluid from the injection port to the upper portion of the drive housing.

2. The surgical tool of claim 1, wherein the injection port is a dual injection port.

3. The surgical tool of claim 2, wherein the dual injection port has a first port and second port.

4. The surgical tool of claim 3, wherein the first port and second port are in the lower portion of the drive housing.

5. The surgical tool of claim 4, wherein the first port passes fluid into the drive housing and the second port passes fluid into the elongated shaft.

6. The surgical tool of claim 5, wherein the second port is below the ramp and the first port is above the ramp.

7. The surgical tool of claim 1, wherein the diverter has a flat portion contained within the upper portion of the drive housing and coupled to the ramp.

8. The surgical tool of claim 7, wherein the diverter has a wall adjacent to and extending above the ramp and said flat portion.

9. The surgical tool of claim 8, wherein the wall has a curve that wraps around the flat portion opposite of the ramp.

10. The surgical tool of claim 9, wherein the curve portion is between forty-five and one hundred and thirty-five degrees.

11. The surgical tool of claim 2, further comprising a third port that passes fluid into the drive housing.

12. The surgical tool of claim 11, wherein the third port is orthogonal to said first port and second port.

13. A method of cleaning a robotic surgical tool, comprising:

attaching an injection mechanism to an injection port that passes fluid into the surgical tool;

injecting a fluid into the surgical tool through the port, the surgical tool including:

a plate;

a drive housing, divided into an upper portion and lower portion by the plate;

an elongated shaft extending from the drive housing; and a diverter inside the drive housing adjacent to the injection port, the diverter including a ramp;

diverting the fluid from the injection port with the ramp to the upper portion of the drive housing;

filling the upper portion and lower portion of the drive housing with fluid from the injection port; and draining the cleaning solution from the drive housing.

14. The method of claim 13, wherein the injection port is a dual injection port.

15. The method of claim 14, wherein the dual injection port has a first port and second port.

16. The method of claim 15, wherein the first port passes fluid into the drive housing and the second port passes fluid into the elongated shaft.

17. The method of claim 16, wherein the second port is below the ramp and the first port is above the ramp.

18. The method of claim 13, further comprising a third port that passes fluid into the drive housing.

19. The method of claim 18, wherein the third port is orthogonal to said first port and second port.

20. The method of claim 19, wherein third port also serves as a drain for draining the fluid.

\*    \*    \*    \*    \*